United States Patent [19]
Tsurita et al.

[11] Patent Number: 5,530,144
[45] Date of Patent: Jun. 25, 1996

[54] PROCESS FOR PRODUCING A PHOSPHORUS-VANADIUM OXIDE CATALYST PRECURSOR, PROCESS FOR PRODUCING A PHOSPHORUS-VANADIUM OXIDE CATALYST, AND PROCESS FOR PRODUCING MALEIC ANHYDRIDE BY VAPOR PHASE OXIDATION USING THE CATALYST

[75] Inventors: Yasushi Tsurita, Kurashiki; Masayoshi Murayama, Yokohama; Kenji Shima, Yokohama; Masumi Ito, Yokohama, all of Japan

[73] Assignee: Mitsubishi Chemical Corporation, Tokyo, Japan

[21] Appl. No.: 359,596

[22] Filed: Dec. 20, 1994

[30] Foreign Application Priority Data

Dec. 22, 1993 [JP] Japan ................... 5-324273
Dec. 22, 1993 [JP] Japan ................... 5-324274

[51] Int. Cl.$^6$ .............. C07D 307/34; C07D 307/36; B01J 27/198; C01B 15/16
[52] U.S. Cl. .............. 549/259; 549/262; 502/150; 502/167; 502/172; 502/209; 502/210; 502/213; 423/305; 423/306
[58] Field of Search .............. 549/262, 259; 502/209, 210, 213, 150, 167, 172; 423/305, 306

[56] References Cited

U.S. PATENT DOCUMENTS

| 4,132,670 | 1/1979 | Katsumoto et al. |
| 4,317,778 | 3/1982 | Blum et al. |
| 4,333,853 | 6/1982 | Milberger et al. |
| 4,351,773 | 9/1982 | Milberger et al. |
| 4,365,069 | 12/1982 | Bremer et al. |
| 4,374,043 | 2/1983 | Blum et al. |
| 4,472,527 | 9/1984 | Otake et al. |
| 4,520,127 | 5/1985 | Otake et al. |
| 4,647,673 | 3/1987 | Bremer et al. |
| 5,021,384 | 6/1991 | Hatano et al. ............ 502/209 |
| 5,128,299 | 7/1992 | Hatano et al. ............ 502/209 |

FOREIGN PATENT DOCUMENTS

0107274A1  5/1984  European Pat. Off.

*Primary Examiner*—Cecilia Tsang
*Attorney, Agent, or Firm*—Oblon, Spivak, McClelland, Maier & Neustadt

[57] ABSTRACT

A process for producing a precursor of a phosphorus-vanadium oxide catalyst for production of maleic anhydride by vapor phase oxidation of a hydrocarbon having 4 carbon atoms, which comprises reacting phosphoric acid and a pentavalent vanadium compound in an organic solvent capable of reducing at least a portion of the pentavalent vanadium to a valence state of +4, the phosphoric acid being substantially composed of orthophosphoric acid, and a phosphoric acid solution whose concentration is 88 to 96% being used as a source of the phosphoric acid; and a process for producing the catalyst comprising dry-pulverizing the catalyst precursor.

27 Claims, No Drawings

PROCESS FOR PRODUCING A PHOSPHORUS-VANADIUM OXIDE CATALYST PRECURSOR, PROCESS FOR PRODUCING A PHOSPHORUS-VANADIUM OXIDE CATALYST, AND PROCESS FOR PRODUCING MALEIC ANHYDRIDE BY VAPOR PHASE OXIDATION USING THE CATALYST

BACKGROUND OF THE INVENTION

The present invention relates to a process for producing a phosphorus-vanadium oxide catalyst precursor, a process for producing a phosphorus-vanadium oxide catalyst, and a process for producing maleic anhydride by vapor phase oxidation using the catalyst, and particularly the present invention relates to an improved process for producing a catalyst precursor composed of phosphorus-vanadium oxide for production of a catalyst which is useful in the production of maleic anhydride by vapor oxidation of a hydrocarbon having 4 carbon atoms such as butane, butene and butadiene, and an improved process for producing the catalyst.

Catalysts containing tetravalent vanadium and pentavalent phosphorus have been used for production of maleic anhydride by selective oxidation in a vapor phase of a hydrocarbon having 4 carbon atoms such as butane, butene, butadiene or the like, especially n-butane which is a saturated hydrocarbon. There is much literature on vanadyl pyrophosphate ($(VO)_2P_2O_7$) known as a crystalline mixed oxide catalyst having excellent catalytic performance (see, for example, Chem. Rev. 88, p. 55–80 (1988) and references cited therein). Concerning synthesis of the vanadyl pyrophosphate, it has been reported that its precursor, phosphorus-vanadium oxide, specifically vanadyl hydrogen phosphate hemihydrate ($VOHPO_4 \cdot 0.5H_2O$) can be converted into vanadyl-pyrophosphate through topotactic transformation on calcination.

Many proposals have been made on the production of the precursor, vanadyl hydrogen phosphate hemihydrate. Most of them employ a process for producing the precursor in an organic solvent, which comprises reducing at least a portion of a pentavalent vanadium compound in an organic solvent and then reacting it with a pentavalent phosphorus compound to obtain a composite oxide of pentavalent phosphorus and tetravalent vanadium.

For example, Japanese Patent Publication (KOKOKU) No. 57-8761 (1982) and U.S. Pat. No. 4,132,670 disclose a process in which vanadium of vanadium pentoxide is reduced to a valence of 4.0 to 4.6 in a substantially anhydrous organic solvent and then reacted with orthophosphoric acid. The orthophosphoric acid source used in each of the Examples of the publications is specifically 100% orthophosphoric acid in isobutyl alcohol or 85% phosphoric acid.

Japanese Patent Publication (KOKOKU) No. 1-50455 (1989) discloses production of a catalyst precursor by heating substantially a pentavalent vanadium compound and a phosphorus-containing compound in a saturated organic solvent. In the Examples, 100% orthophosphoric acid in isobutanol is used.

Japanese Patent Publication (KOKOKU) Nos. 2-97 (1990) and 2–98 (1990) and U.S. Pat. Nos. 4,374,043 and 4,317,778 disclose production of vanadium phosphorus oxide catalyst precursors using a mixed phosphorus source. The "mixed phosphorus source" refers to a mixture of orthophosphoric acid, pyrophosphoric acid and a small amount of triphosphoric acid. Specifically, a mixture of 75–90% by weight of orthophosphoric acid and 10–25% by weight of pyrophosphoric acid is used.

Japanese Patent Publication (KOKOKU) No. 62-61951 (1987) and U.S. Pat. Nos. 4,3.65,069 and 4,448,873 disclose production of vanadium phosphorus oxide catalyst precursors using an organic solvent as reaction medium, wherein a portion of the organic solvent is distilled out from the system during the reaction. The used phosphorus source is 85% orthophosphoric acid or a mixed phosphorus source of a composition such as mentioned above.

Industrially, with respect to the reaction for the production of maleic anhydride by vapor phase oxidation of a hydrocarbon, attention is recently focused on use of fluid bed catalysts in place of conventional fixed bed catalysts, and some proposals have already been made regarding the process for producing fluid bed catalysts. For example, Japanese Patent Application Laid-Open (KOKAI) No. 57-122944 (1982) and U.S. Pat. No. 4,351,773 disclose a process which comprises comminuting the catalyst precursor prepared in an organic liquid, introducing the precursor into water to form an aqueous slurry, and then spray-drying the slurry. As the catalysts usable for the reaction, there are shown a catalyst using a catalyst precursor synthesized by using 100% phosphoric acid-or a mixed phosphoric acid in an organic solvent and a catalyst obtained by mixing the precursor with silica. As means for comminuting the catalyst precursor, ball milling is merely mentioned.

Japanese Patent Application Laid-Open (KOKAI) No. 59-55350 (1984) and U.S. Pat. No. 4,647,673 propose a process for producing the fluid bed oxidation catalyst by densification and comminution of the precursor containing a mixed oxide of vanadium and phosphorus to form the fluidisable particles and then calcining these particles under the fluidization conditions. In the Examples of these publications, it is shown that the comminution of the precursor is effected by a ball mill to form an aqueous slurry, followed by spray drying with or without addition of silica sol. It is taught that catalyst strength is unsatisfactory when the comminution is performed by an air mill.

Japanese Patent Application Laid-Open (KOKAI) No. 60-64632 (1985) discloses a process in which a crystalline composite oxide containing tetravalent vanadium and pentavalent phosphorus and obtained by reacting a pentavalent vanadium compound and a pentavalent phosphorus compound in an organic solvent capable of reducing the pentavalent vanadium to a tetravalent state, as the first component; an aqueous solution containing tetravalent vanadium and phosphorus, as the second component; and silica sol as the third component are mixed to prepare an aqueous slurry followed by spray drying thereof. In the Examples of the publication, the three-component mixed slurry is subjected to wet pulverizing and mixing, then spray dried and calcined to form a fluid bed catalyst.

Although there are the vanadium/phosphorus oxide catalysts produced by the known methods including those mentioned above, it is still desired to establish a maleic anhydride production process which can balance at a higher level, all of the following requirements: (1) high yield of maleic anhydride; (2) high performance at a low reaction temperature and long life of the catalyst; (3) high mechanical strength of the catalyst; (4) good reproducibility of the production process.

Under the circumstance, the present inventors have made extensive studies and have found that a maleic anhydride production process which has a high yield even at a lower temperature and keeps excellent reaction results for longer time, can be provided by using an aqueous phosphoric acid of a specified concentration in the preparation of catalyst precursors. The above-mentioned finding is surprising because as the phosphoric acid, 85% phosphoric acid has been used due to good availability on an industrial scale and low cost, or solid phosphoric acid (e.g. 100% orthophosphoric acid) has been used due to knowledge of skilled persons that an anhydrous medium is preferable in the production of the phosphorus-vanadium oxide catalyst (for example, see U.S. Pat. No. 4,132,670, col. 6, p. 47–54). Further, the present inventors have found that the above four requirements are satisfied at a higher level by dry-pulverizing the said catalyst precursor in a high-speed gas flow. The present invention has been attained on the basis of these findings.

SUMMARY OF THE INVENTION

An object of the present invention is to provide a catalyst precursor for manufacture of a catalyst suited for production of maleic anhydride by vapor phase oxidation of a hydrocarbon having 4 carbon atoms, and a process for producing the catalyst by using the said precursor.

Another object of the present invention is to provide a process for producing maleic anhydride using the catalyst.

In the first aspect of the present invention, there is provided a process for producing a precursor of a phosphorus-vanadium oxide catalyst for production of maleic anhydride by vapor phase oxidation of a hydrocarbon having 4 carbon atoms, which comprises reacting phosphoric acid and a pentavalent vanadium compound in an organic solvent capable of reducing at least a portion of the pentavalent vanadium to a valence state of +4, the phosphoric acid being substantially composed of orthophosphoric acid, and a phoshoric acid solution whose concentration is 88 to 96% being used as a source of the phosphoric acid.

An the second aspect of the present invention, there is provided a process for producing a phosphorus-vanadium oxide catalyst for production of maleic anhydride by vapor phase oxidation of a hydrocarbon having 4 carbon atoms, which comprises the steps of (1) reacting phosphoric acid and a pentavalent vanadium compound in an organic solvent capable of reducing at least a portion of the pentavalent vanadium to a valence state of +4, the phosphoric acid being substantially composed of orthophosphoric acid, and a phoshoric acid solution whose concentration is 88 to 96% being used as a source of the phosphoric acid, to produce a catalyst precursor; (2) dry-pulverizing the catalyst precursor in a high-speed gas flow; and (3) mixing the pulverized material with an aqueous solution containing phosphorus and tetravalent vanadium to form a slurry, and drying the slurry and calcining.

In the third aspect of the present invention, there is provided a process for producing maleic anhydride by vapor phase oxidation of a hydrocarbon having 4 carbon atoms in the presence of a catalyst produced by using a phosphorus-vanadium oxide catalyst precursor obtainable by reacting phosphoric acid and a pentavalent vanadium compound in an organic solvent capable of reducing at least a portion of the pentavalent vanadium to a valence state of +4, the phosphoric acid being substantially composed of orthophosphoric acid, and a phoshoric acid solution whose concentration in 88 to 96% being used as a source of the phosphoric acid.

DETAILED DESCRIPTION OF THE INVENTION

First, the process for producing a catalyst precursors according to the present invention is described.

Preferred pentavalent vanadium compounds for use as a starting material of the catalyst precursor are vanadium pentoxide and vanadium salts such as ammonium metavanadate and vanadium oxytrihalides. Vanadium pentoxide is most preferably used. A commercially available product of this compound may be used in the form as it is or in a pulverized state.

The phosphoric acid used as another starting material of the catalyst precursor is substantially composed of orthophosphoric acid, in other words, it contains substantially no other type of phosphoric acid such as pyrophosphoric acid and triphosphoric acid. In the process of the present invention, phosphoric acid is used in the form of an aqueous solution with a high concentration in the range of 88 to 96% calculated as orthophosphoric acid. (Percentages (%) shown here and hereinafter are by weight unless otherwise noted.) As the phosphoric acid, commercial 89% phosphoric acid which may be used in the form as it is, or the phosphoric acid may be prepared from commercial 85%, 89% or 105% phosphoric acid. There are available several preparation methods for the phosphoric acid, such as: (1) water is added to 105% phosphoric acid; (2) 85% or 89% phosphoric acid and 105% phosphoric acid are mixed together in an appropriate ratio; (3) water is removed from 85% or 89% phosphoric acid. Method (1) or (2) is preferred. A method is also employable in which water is added to 99% or 100% (purity) phosphoric acid which is available as a white solid reagent, but this type of phosphoric acid is costly and handling thereof is hard as it is solid.

The percentage in "105% phosphoric acid" represents the concentration of phosphoric acid in an aqueous solution calculated as orthophosphoric acid basis, so that 105% phosphoric acid is actually a mixture of orthophosphoric acids, pyrophosphoric acid and triphosphoric acid. In the above methods (1) and (2), the phosphorus sources other than orthophosphoric acid in the mixed phosphoric acid are reacted with water to provide a phosphoric acid which is substantially composed of orthophosphoric acid alone, and this form of phosphoric acid is used.

It is possible to use 116% phosphoric acid, a further condensed version of phosphoric acid, but its use is unfavorable because preparation of the phosphoric acid with the specific concentration used in the present invention from this type of phosphoric acid is time-consuming.

The expression of "substantially composed of orthophosphoric acid" used herein means that a proportion of orthophosphoric acid is not less than 99 mol % based on the whole phosphoric acid.

In the present invention, a catalyst precursor is prepared by using an aqueous phosphoric acid solution substantially composed of orthophosphoric acid with a specific concentration as mentioned above, and a catalyst is produced from the precursor by a specific process, the finally obtained catalyst being notably improved in catalytic characteristics.

The ratio of phosphoric acid to pentavalent vanadium compound is preferably 1.0:1 to 1.3:1 in terms of phosphorus to vanadium atomic ratio.

The organic solvent used in the present invention has in itself a reducing action. The reducing organic solvents usable in the present invention include those having functional groups which are susceptible to oxidation, preferably the compounds having alcoholic hydroxyl groups. Typical examples of such compounds are aliphatic alcohols having 3 to 6 carbon atoms, such as butanol, 2-propanol, 2-methylpropanol and hexanol, and benzyl alcohol. It is possible to use a mixture thereof as the organic solvent. For example, a mixture of an aliphatic alcohol having 3 to 6 carbon atoms and benzyl alcohol having a high reducing power is preferably used. A reducing agent such as hydrazine or oxalic acid may be present in the organic solvent. The amount of the organic solvent is not specified provided that its amount is sufficient to serve as a reaction medium, but in case of using benzyl alcohol as a solvent component, the molar ratio of benzyl alcohol to the pentavalent vanadium compound is usually 0.02:1 to 2:1, preferably 0.5:1 to 1.5:1. A catalyst with especially high activity can be obtained when the materials are used in the above-defined amount range.

The catalyst produced according to the process of the present invention may contain metal elements as a cocatalyst. The cocatalyst metals that can be added to the reaction system and contained in the catalyst precursor include iron, cobalt, zinc and the like. These metals may be added in combination. Iron is preferred for use in the process of the present invention. The cocatalyst metal is preferably incorporated as a compound in the reaction medium in the production of the precursor. Examples of such compounds are ferrous chloride, ferrous acetate, ferrous oxalate and the like. In case of using a Cocatalyst metal such as iron, the atomic ratio of the cocatalyst metal to the sum of vanadium and cocatalyst metal is usually 0.005:1 to 0.3:1, preferably 0.02:1 to 0.2:1.

In the process of the present invention, a slurry containing the above-mentioned materials is formed and this slurry is reacted, ordinarily with stirring under heating, to produce the phosphorus-vanadium mixed oxide as particles.

Embodiments of the process of the present invention include a process in which a pentavalent vanadium compound, preferably vanadium pentoxide, is first heated under reflux in a reducing organic solvent to reduce a portion of the vanadium to a valence of +4 and then phosphoric acid is added, and a process in which a pentavalent vanadium compound and phosphoric acid are directly mixed at the beginning of the reaction, but the former process is preferred.

In case of using a cocatalyst metal compound, it may be added either at the beginning of the reaction or after addition of phosphoric acid.

Heating of the slurry formed by mixing the materials is usually carried out at a temperature in the range of 80° to 200° C. although it is dependent on the type of the organic solvent used. Preferably the mixture is refluxed at a temperature close to the boiling point of the solvent used. The heating time is variable depending on the reaction conditions but usually 1 to 20 hours after addition of phosphoric acid to the reaction system.

In some cases, water in the materials or water generated from the reaction is preferably removed in the course of reaction (during heating and/or refluxing), as performance of the produced catalyst tends to be high. In this case, although there is no need of removing substantially the whole amount of water in the reaction system, it is preferable to conduct continuous removal of water. The organic solvent evaporated along with water by heating, when condensed by cooling, is separated into an organic layer and an aqueous layer. The organic layer is returned to the reaction system while the aqueous layer is removed. This operation can be easily performed by using, for instance, a Dean-Stark apparatus.

The mixed oxide particles obtained in the manner described above contain vanadyl hydrogen phosphate hemihydrate and may not necessarily be completely crystalline. The particles are separated by using an ordinary solid-liquid separating means and, if necessary, washed with solvent such as alcohol.

The thus produced catalyst precursor may be calcined by heating in the form as it is or after molded using a known binder or carrier, to convert at least a portion of vanadyl hydrogen phosphate hemihydrate in the catalyst precursor to an active compound, vanadyl pyrophosphate, thus producing a catalyst.

The catalyst producing process according to the present invention comprises the steps of preparing a catalyst precursor in the manner described above (first step), dry-pulverizing the catalyst precursor in a high-speed gas flow (second step), and mixing the pulverized material with an aqueous solution containing phosphorus and tetravalent vanadium to form a slurry, and drying the resultant slurry and calcining (third step).

In the present invention, it is preferred that the catalyst precursor particles obtained in the first step are not calcined and are subjected to the operation-in the second step in a dry state.

The pulverizing of the particles is effected by impingement of the particles against each other or against a wall of a pulverizing apparatus by a high-speed gas flow. The high-speed gas flow can be easily formed by, for example, blowing a gas from a nozzle. There can be used air and various types of inert gas, as the gas source. Air is preferable for economical reason. An example of the pulverizing apparatus is a jet mill known in the field of powder working (see Handbook of Micromeritics, edited by Japan Society of Micromeritics and published by Nikkan Kogyo Shinbunsha, Feb. 28, 1986 (1st ed.)). Examples of the Jet mill are jet ohmizer mill and single-track jet mill. The jet-mill type pulverizing apparatus is preferred as it is capable of continuous pulverizing with ease on an industrial scale. According to the studies by the present inventors, it has been found that the precursor particles obtained in the first step in the process of the present invention can be broken relatively easily to particles having a weight-average particle size of not more than 3 μm by the dry pulverizing in a high-speed gas flow.

The gas pressure in jet mill pulverizing depends on the way of producing the precursor in the first step and pulverizing rate (material feed rate), but it is preferably 3 to 10 KG ($kg/cm^2$-G, gage pressure). When the gas pressure is below 3 KG, the produced fluid bed catalyst may be unsatisfactory in strength, and when the gas pressure exceeds 10 KG, high-pressure equipment is required. The particle size of the particles obtained in the second step is preferably in the range of 0.5 to 2.0 μm in terms of weight-average particle size, although it is variable depending on the properties of the particles obtained the first step and the pulverizing conditions in the second step.

Dry pulverizing in a high-speed gas flow is preferred because of no fear of contamination of the material of the pulverizing medium due to its abrasion, thus preventing unfavorable effects on catalytic performance, unlike in the conventional dry or wet milling by a ball mill or the like. Also, it is unnecessary to separate the medium and the pulverized material, which substantially reduce the treating time and allows continuous pulverizing operation. Further, drying can be accomplished simultaneously by dry pulverizing in a high-speed gas flow:

Also, dry pulverizing in a high-speed gas flow, as compared with conventional dry ball milling, provides a sharper particle size distribution because contamination of coarse particles can be prevented. Usually, therefore, by this pulverizing system, a particle size distribution with good reproducibility can be easily obtained although it affected by some factors such as the shape of the particles produced in the first step and the pulverizing conditions in the second step. For instance, the ratio of 25% diameter ($d_{25}$) to 75% diameter ($d_{75}$), $d_{25}/d_{75}$ is usually not more than 6, preferably not more than 5, wherein $d_{25}$ is a particle diameter at the point of 25% of the total accumulated weight and $d_{75}$ is a particle diameter at the point of 75%, when the weights of the particles classified are accumulated in order of size. The value is small in comparison with that provided by other ordinary dry pulverizing means such as ball milling.

Also, comparison of the powder X-ray diffraction patterns (source: CuK α-rays).before and after dry pulverizing in a high-speed gas flow shows that the ratio of strength at 2θ=15.5° to strength at 2θ=30.4° is changed and the peak at 15.5° is intensified. This peak at 15.5° corresponds to the 001 plane (broad plane of the plate crystal) of the catalyst precursor, vanadyl hydrogen phosphate hemihydrate. This change of peak strength indicates that the catalyst precursor has been deagglomerated and converted to the plate like state. It is considered that such transformation of shape of the catalyst precursor is effective to the improvement of mechanical strength of the catalyst.

In the third step, the pulverized particles obtained in the second step are mixed with an aqueous solution containing phosphorus and tetravalent vanadium to form an aqueous slurry, and this slurry is dried and calcined to obtain a catalyst. As the aqueous solution, there is preferably used a solution which is capable of forming an aqueous slurry and can be acidified, such as an aqueous solution of vanadyl phosphate.

The aqueous solution of vanadyl phosphate is a stabilized solution containing substantially tetravalent vanadium and phosphorus. For instance, the solution disclosed in Japanese Patent Application Laid-Open (KOKAI) No. 58-151312 (1983) can be used. The aqueous solution may be obtained by reacting a pentavalent vanadium compound such as vanadium pentoxide with a reducing agent such as hydrazine hydrate, phosphorous acid, lactic acid or the like in an acidic aqueous solution of phosphoric acid to reduce the pentavalent vanadium to tetravalent vanadium, and further adding oxalic acid or allowing it to remain in the reaction system for stabilization. The amount of oxalic acid in the solution is not more than 1.2, preferably 0.2 to 1, in terms of a molar ratio to vanadium. The amount of phosphorus is preferably 0.5 to 10 in molar ratio to vanadium.

Since the aqueous solution is stabilized, it can be previously prepared for industrial applications. Preferably, the pulverized particles obtained in the second step are added to the aqueous solution to form an aqueous slurry. The concentration (solid content) of the aqueous slurry is preferably in the range of 10 to 50% in terms of the weight basis of the oxide catalyst after calcination. When the concentration is below 10%, the drying efficiency may lower, and when the concentration exceeds 50%, the slurry viscosity may raise to make the slurry unsuited for spray drying. It is considered that this vanadyl phosphate solution, when dried and calcined, becomes an amorphous vanadium-phosphorus oxide to serve as a binder component that develop mechanical strength of the catalyst. It is preferable that the pulverized particles obtained in the second step are mixed with the vanadyl phosphate aqueous solution in such a way that the weight percentage of the component A in the catalyst after calcination is in the range of 80 to 50% and that of the component B is in the range of 20 to 50%, when the amorphous vanadium-phosphorus oxide is expressed as component B and the pulverized particles obtained in the second step after dried and calcined are expressed as component A.

Silica such as fumed silica or silica sol may be added to the slurry, preferably in an amount of not more than 10% by weight in the catalyst after calcination. Silica may not necessarily be added in the present invention.

The aqueous slurry is molded into an appropriate form for catalyst and then dried, or molded after dried, or dried while molding as by spray drying, followed by calcination.

Drying can be effected by conventional methods such as spray drying or heating. In case of forming the microspherical solid particles suited as fluid bed catalyst or transport bed reaction catalyst, rotary disc-type or nozzle-blowing-type spray drying is preferably employed. By this method, solid particles having an average size of about 20 to 300 μm Can be formed. The drying temperature is preferably in the range of 100° to 350° C., more preferably 100° to 250° C. The molding method is not specified as far as the particles with a size of not bigger than around 300 μm suited for fluid bed catalysts can be formed. The spray dried solid particles usually have a size in the above-defined range, so they needn't be molded and can be immediately subjected to calcination. In the case of fixed bed catalyst, known pelletizing or tableting methods such as extrusion molding can be employed.

The solid particles obtained from the drying and molding operations are then calcined to produce the objective catalyst particles. Calcination is usually carried out under an atmosphere of nitrogen, rare gas, air, mixture thereof, or a reaction gas such as air containing a hydrocarbon having 4 carbon atoms such as butane or butene, at a calcination temperature of 350° to 700° C. for 0.1 to 20 hours. Various types of calcining or firing devices such as fluid furnace, kiln-type furnace, continuous box-type furnace, etc., can be used.

In the present invention, as described above, the precursor obtained in the first step is subjected to the treatments in the second and third steps and, if necessary, to a succeeding activation treatment, so as to convert at least a portion of the vanadyl hydrogen phosphate hemihydrate in the precursor to vanadyl pyrophosphate which is the active ingredient of catalyst, thus producing the objective catalyst.

The catalyst described above can be favorably used for the production of maleic anhydride by vapor phase oxidation of a hydrocarbon having 4 carbon atoms such as n-butane, 1-butene, 2-butene, 1,3-butadiene or the like. Of these hydrocarbon sources, n-butane and butene are economically advantageous as they are easily obtainable by separation from natural gases or naphtha cracking products. The oxidation reaction may be fluid bed-type, fixed bed-type or transport bed-type, but the process of the present invention is especially suited for producing fluid bed catalysts. As the oxidizing agent in the production of maleic anhydride, air or a gas containing oxygen such as molecular oxygen can be used. In the above oxidation reaction, the hydrocarbon concentration is usually 0.1 to 10 vol %, preferably 1 to 5 vol %, and the oxygen concentration is 10 to 30 vol % based on the total amount of the hydrocarbon and the oxygen-containing gas. The reaction is carried out at a temperature of usually 300° to 500° C., preferably 350° to 450° C., under normal pressure or under a pressure of 0.05 to 10 kg/cm$^2$-G.

The crystalline composite oxide particles obtained in the first step, are a precursor for producing a catalyst having advantages in catalytic activity, reaction conditions, etc. When the particles are dry pulverized in a high-speed gas flow and mixed with an aqueous solution containing tetravalent vanadium and phosphorus to form a slurry, and this slurry is spray dried and calcined, an oxide catalyst remarkably improved in mechanical strength and particle fluidity and capable of providing the excellent reaction results can be produced at low cost and with good reproducibility even under the industrial catalyst producing conditions.

Such effects of the present invention is considered attributable to the fact that the particle size distribution is made sharp, facilitating enhancement of mechanical strength of the particles, by dry pulverizing in a high-speed gas flow in the second step as compared with conventional dry comminuting means such as ball milling. Also, it is considered that tetravalent vanadium and pentavalent phosphorus in the aqueous slurry obtained in the third step becomes an amorphous vanadium-phosphorus oxide in the catalyst produced after drying and calcination, and this oxide serves as a binder component which derives the catalyst strength. Such binder effect provides a remarkable improvement.

The catalyst produced by using the phosphorus-vanadium oxide; catalyst precursors produced according to the process of the present invention provide a high yield of reaction product even in a relatively low temperature range and can maintain good reaction performance for a long time in the reaction for producing maleic anhydride by the selective oxidation of a hydrocarbon having 4 carbon atoms, especially saturated butane. Accordingly, the production rate of maleic anhydride per catalyst is increased, and a unit amount of catalyst can be reduced. Further, according to the catalyst production process of the present invention, the catalyst can be produced with good reproducibility under the industrial production conditions, and the produced catalyst has excellent mechanical strength. In the production on the industrial scale, improvement of a selectivity or yield have great significance, even if a few percent.

EXAMPLES

The present invention is described in more detail below with reference to examples thereof. It is to be understood, however, that these examples are merely intended to be illustrative and not to be construed as limiting the scope of the invention.

"Percent (%)" in Examples is "% by weight" unless otherwise noted. Also, "n % phosphoric acid" means an aqueous phosphoric acid solution in which the concentration of the whole phosphoric acid sources calculated as orthophosphoric acid is n %, unless otherwise noted.

Reference Example

Each ratio of orthophosphoric acid to pyrophosphoric acid in phosphoric acid preparations of a predetermined concentration was determined from a nuclear magnetic resonance spectrum of phosphorus ($^{31}$P-NMR). 100% Phosphoric acid and 94% phosphoric acid were prepared by adding water to commercial 105% phosphoric acid. The results of the determination are shown in the following. 94% Phosphoric acid contains substantially no pyrophosphoric acid.

|  | Orthophosphoric acid/ pyrophosphoric acid (molar ratio) |
|---|---|
| (1) 105% phosphoric acid | 71.3/28.7 |
| (2) 100% phosphoric acid | 97.9/2.1 |
| (3) 94% phosphoric acid | 99.9/0.1 |

Example 1

46.9 g of water was added to 448.3 g of 105% phosphoric acid and heated at about 100° C. for 2 hours to prepare 95% phosphoric acid. This obtained phosphoric acid was substantially composed of orthophosphoric acid alone. Separately, 2,195 g of 2-methylpropanol, 205.4 g of benzyl alcohol, 347.5 g of vanadium pentoxide and 36.0 g of ferrous oxalate dihydrate were placed in a 10-liter vessel and heated under reflux in a slurry state for 3 hours. To this slurry was added a solution of the 95% phosphoric acid in 1.0 liter of 2-methylpropanol as a phosphoric acid source, followed by addition of 2.4 liters of 2-methylpropanol. This slurry was further heated under reflux for 7 hours and then cooled. The resultant product was washed with 2-methylpropanol, filtered and dried at 130° C. for 10 hours to produce a catalyst precursor.

Example 2

95% Phosphoric acid was prepared by mixing 248 g of 85% phosphoric acid and 248 g of 105% phosphoric acid and allowing the mixture to stand at room temperature for 24 hours. This 95% phosphoric acid was substantially composed of orthophosphoric acid alone. A catalyst precursor was produced in the same way as Example 1 except that a solution of 496 g of the 95% phosphoric acid in 1.0 liter of 2-methylpropanol was used as a phosphoric acid source.

Example 3

From a solution consisting of 528.5 g of 89% phosphoric acid and 1,610 g of 2-methylpropanol, parts of water and 2-methylpropanol were removed by azeotropic distillation to prepare a solution corresponding to 95% phosphoric acid in 2-methylpropanol. The phosphoric acid in the obtained solution was substantially composed of orthophosphoric acid alone. 2-Methylpropanol was added to this solution, making the total amount of the solution to 1,800 g. A catalyst precursor was produced in the same way as Example 1 except for use of the solution as a phosphoric acid source and addition of 1.8 liters of 2-methylpropanol.

Example 4

954 Phosphoric acid was prepared by removing water from a mixed solution of 85% phosphoric acid and 2-methylpropanol by azeotropic distillation. This 95% phosphoric acid was substantially composed of orthophosphoric acid alone. 3,672 g of 2-methylpropanol and 365.8 g of vanadium pentoxide were placed in a 10-liter vessel and 495.2 g of the 95% phosphoric acid in 1.0 liter of 2methylpropanol as a phosphoric acid source were added. The resultant slurry was heated under reflux for 7 hours and then cooled. The resultant product was washed with 2-methylpropanol, filtered and dried at 130° C. for 10 hours to produce a catalyst precursor.

Example 5

95% Phosphoric acid was prepared by adding 2.4 g of water to 22.4 g of 105% phosphoric acid and stirring the mixture at room temperature for one day. This 95% phosphoric acid was substantially composed of orthophosphoric acid alone. This 95% phosphoric acid was placed in a 0.5 liter vessel, and then 152.0 g of 2-methylpropanol, 10.8 g of benzyl alcohol, 17.4 g of vanadium pentoxide and 1.8 g of ferrous oxalate dihydrate were added thereto. The resultant slurry was heated under reflux for 7 hours and then cooled.

The resultant product was washed with 2-methylpropanol, filtered and dried at 130° C. for 10 hours to produce a catalyst precursor.

Example 6

96% Phosphoric acid was prepared by removing water from a mixed solution of 85% phosphoric acid and 2-methylpropanol by azeotropic distillation. This 96% phosphoric acid was substantially composed of orthophosphoric acid alone. By using this 96% phosphoric acid, a catalyst precursor was produced in the same way as Example 5.

Comparative Example 1

2,400 g of 2-methylpropanol and 347.5 g of vanadium pentoxide were placed in a 10-liter vessel and heated under reflux in a slurry state for 3 hours. To this slurry was added a solution of 553.4 g of 85% phosphoric acid in 1.0 liter of 2-methylpropanol, followed by addition thereto of a suspension of 36.0 g of ferrous oxalate dihydrate in 2.4 liters of 2-methylpropanol. The resultant slurry was heated under reflux for 7 hours and then cooled. The resultant product was washed with 2-methylpropanol, filtered and dried at 130° C. for 10 hours to produce a catalyst precursor.

Comparative Example 2

2,400 g of 2-methylpropanol, 347.5 g of vanadium pentoxide and 36.0 g of ferrous oxalate dihydrate were placed in a 10-liter vessel and refluxed. Then, to the resultant slurry was added a solution of 475.2 g of solid phosphoric acid (purity: 99%, a reagent produced by Merck & Co., Ltd. ), in 3.4 liters of 2-methylpropanol. This slurry was heated under reflux for 7 hours and then cooled. The resultant product was washed with 2-methylpropanol, filtered and dried at 130° C. for 10 hours to produce a catalyst precursor.

Comparative Example 3

2,400 g of 2-methylpropanol, 347.5 g of vanadium pentoxide and 36.0 g of ferrous oxalate dihydrate were placed in a 10-liter vessel and heated under reflux in slurry state for 3 hours. To this slurry was added a solution of 475.2 g of solid phosphoric acid (purity: 99%) in 1.0 liter of 2-methylpropanol, followed by additional supply of 2-methylpropanol. This slurry was heated under reflux for 7 hours and then cooled. The resultant product was washed with 2-methylpropanol, filtered and dried at 130° C. for 10 hours to produce a catalyst precursor.

Comparative Example 4

2,400 g of 2-methylpropanol and 365.8 g of vanadium pentoxide were placed in a 10-liter vessel and refluxed. On the beginning of reflux, a solution of 553.4 g of 85% phosphoric acid in 1.0 liter of 2-methylpropanol was added, followed by supply of 2.4 liters of 2-methylpropanol. This slurry was heated under reflux for 7 hours and then cooled. The resultant product was washed with 2-methylpropanol, filtered and dried at 130° C. for 10 hours to produce a catalyst precursor.

Comparative Example 5

2,400 g of 2-methylpropanol and 365.8 g of vanadium pentoxide were placed in a 10-liter vessel and refluxed. On the beginning of reflux, a solution of 475.2 g of solid phosphoric acid (purity: 99%) in 1.0 liter of 2-methylpropanol was added, followed by supply of 2.4 liters of 2-methylpropanol. This slurry was heated under reflux for 7 hours and then cooled. The resultant product was washed with 2-methylpropanol, filtered and dried at 130° C. for 10 hours to produce a catalyst precursor.

Comparative Example 6

4,904 g of 2-methylpropanol, 216.2 g of benzyl alcohol, 365.8 g of vanadium pentoxide and 475.2 g of solid phosphoric acid (purity: 99%) were placed in a 10-liter vessel. The resultant slurry was heated under reflux for 7 hours and cooled. The resultant product was washed with 2-methylpropanol, filtered and dried at 130° C. for 10 hours to produce a catalyst precursor.

Comparative Example 7

A phosphoric acid with about 100% concentration was prepared by adding water to 10.5% phosphoric acid. By using this 100% phosphoric acid as a phosphoric acid source, a catalyst precursor was in the same way as Example 5.

Comparative Example 8

A catalyst precursor was produced in the same way as Example 5 except for use of commercial 105% phosphoric acid as a phosphoric acid source.

Reaction Test 1

The oxide catalyst precursors obtained in Examples 1–6 and Comparative Examples 1–8 were calcined at 550° C. under a nitrogen atmosphere and molded into particles of 14–24 mesh in size, and each of the thus produced catalysts was subjected to a catalytic activity test. 1 cc of each catalyst was packed in a quartz-made reaction tube and an air-mixed gas with an n-butane concentration of 4 mol % was passed at a rate (GHSV) of 1,000 $Hr^{-1}$ to carry out the reaction at 400° C. After passage of about 20 hours, the state of the reaction was examined by adjusting the-inside temperature of the reaction tube within the range of 350 to 500° C. The reaction tube outlet gas was sampled and analyzed by an on-line connected gas chromatograph. The results are shown in Table 1. The catalysts of the Examples of the present invention provide a higher yield of maleic anhydride, act even at a lower reaction temperature and give better reaction results compared with the catalysts of the Comparative Examples.

TABLE 1

| | Production conditions | | | | Reaction results | | |
|---|---|---|---|---|---|---|---|
| | Phosphoric acid concent- ration (%) | Ratio of added iron 1) | Ratio of added benzyl alcohol 2) | Pre- reflux time (hr) | Reaction temperature 3) (°C.) | n-Butane conversion 4) (%) | Yield of maleic anhydride 5) (%) |
| Example 1 | 95 | 0.05 | 1.0 | 3 | 383 | 91.1 | 54.0 |
| Example 2 | 95 | 0.05 | 1.0 | 3 | 375 | 91.8 | 55.1 |
| Example 3 | 95 | 0.05 | 1.0 | 3 | 366 | 94.0 | 55.7 |
| Example 4 | 95 | 0 | 0 | 0 | 395 | 90.7 | 53.0 |
| Example 5 | 95 | 0.05 | 1.0 | 0 | 390 | 92.3 | 53.8 |
| Example 6 | 96 | 0.05 | 1.0 | 0 | 385 | 90.5 | 52.2 |
| Comp. Example 1 | 85 | 0.05 | 0 | 3 | 386 | 90.0 | 47.0 |
| Comp. Example 2 | Solid | 0.05 | 0 | 0 | 415 | 85.6 | 38.8 |
| Comp. Example 3 | Solid | 0.05 | 0 | 3 | 425 | 83.5 | 37.0 |
| Comp. Example 4 | 85 | 0 | 0 | 3 | 426 | 90.1 | 50.9 |
| Comp. Example 5 | Solid | 0 | 0 | 3 | 405 | 87.9 | 50.7 |
| Comp. Example 6 | Solid | 0 | 1.0 | 0 | 413 | 89.3 | 53.5 |
| Comp. Example 7 | 100 | 0.05 | 1.0 | 0 | — | 65.6 | 21.9 |
| Comp. Example 8 | 105 | 0.05 | 1.0 | 0 | — | 26.7 | 5.5 |

1) Fe/(Fe + V) atomic ratio
2) Benzyl alcohol/vanadium pentoxide molar ratio
3) Reaction temperature at 85% conversion of n-butane
4) Conversion at the time of maximum yield of maleic anhydride
5) Maximum yield of maleic anhydride

Example 7

2,195 g of 2-methylpropanol, 205.4 g of benzyl alcohol, 347.5 g of vanadium pentoxide and 36.0 g of ferrous oxalate dihydrate were placed in a 10-liter vessel and heated under reflux in a slurry state for 3 hours. To this slurry was added a 95% phosphoric acid solution in 2-methylpropanol prepared by adding water to 105% phosphoric acid, and then heating the mixture at 120° C. for one hour, and dissolving it in 1.0 liter of 2-methylpropanol, and then 2.4 liters of 2-methylpropanol was added. The thus prepared 95% phosphoric acid was substantially composed of orthophosphoric acid alone. This slurry was further heated under reflux for 7 hours. During this operation, an aqueous layer portion alone was removed, by a total amount of 54 ml, from the distillate through a Dean-Stark trap. The reaction slurry was cooled, filtered and dried at 130° C. for 10 hours to produce a catalyst precursor.

Example 8

92% Phosphoric acid was prepared and a catalyst precursor was produced in the same way as Example 7. The prepared phosphoric acid was substantially composed of orthophosphoric acid alone. A total 70 ml of aqueous layer was removed during 7-hour heating under reflux.

Comparative Example 9

2,400 g of 2-methylpropanol, 347.5 g of vanadium pentoxide and 553.4 g of 85% phosphoric acid were placed in a 10-liter vessel. The resultant slurry was heated, and on the beginning of reflux, 36.0 g of ferrous oxalate dihydrate was added. The slurry was heated under reflux while removing the aqueous layer by a total amount of 71 ml in the same way as Example 7, thereby producing a catalyst precursor.

Comparative Example 10

5,120 g of 2-methylpropanal, 365.8 g of vanadium pentoxide and 475.2 g of solid phosphoric acid (purity: 99%) were placed in a 10-liter vessel and heated under reflux for 7 hours. During the period of 4 hours from the beginning of reflux, the azeotropic composition of 2-methylpropanol and water was removed by a total amount of 1,450 ml while supplying 1,450 ml of 2-methylpropanol. The resultant slurry was cooled and filtered, and the resultant product was washed with 2-methylpropanol, filtered and dried at 130° C. for 10 hours to produce a catalyst precursor.

Comparative Example 11

A catalyst precursor was produced in the same way as Example 7 except for use of 475.2 g of solid phosphoric acid (purity: 99%). During 7-hour heating under reflux, a total 14.5 ml of the aqueous layer was removed.

Reaction Test 2

The oxide catalyst precursors obtained in Examples 7 and 8 and Comparative Examples 9–11 were calcined under a nitrogen atmosphere at 550° C. and molded into particles of 14–24 mesh in size. The thus produced catalyst particles were subjected to the same catalytic activity test as conducted in Reaction Test 1. The results are shown in Table 2.

TABLE 2

| | Production conditions | | | Reaction results | | |
| --- | --- | --- | --- | --- | --- | --- |
| | Phosphoric acid concentration (%) | Ratio of added iron 1) | Amount of water removed (ml) | Reaction temperature 2) (°C.) | n-Butane conversion 3) (%) | Yield of maleic anhydride 4) (%) |
| Example 7 | 95 | 0.05 | 54 | 382 | 93.0 | 57.4 |
| Example 8 | 92 | 0.10 | 70 | 373 | 92.6 | 55.2 |
| Comp. example 9 | 85 | 0.05 | 71 | 374 | 89.8 | 48.2 |
| Comp. example 10 | Solid | 0 | 65 | 418. | 85.5 | 39.7 |
| Comp. example 11 | Solid | 0.05 | 15 | 412 | 93.5 | 43.3 |

1) Fe/(Fe+ V) atomic ratio
2) Reaction temperature at 85% conversion of n-butane
3) Conversion at the time of maximum yield of maleic anhydride
4) Maximum yield of maleic anhydride

Example 9

2,195 g of 2-methylpropanol, 205.4 g of benzyl alcohol, 347.5 g of vanadium pentoxide and 36.0 g of ferrous oxalate dihydrate were placed in a 10-liter vessel and heated under reflux in a slurry state for 3 hours. To this slurry was added a solution of 528.5 g of 89% phosphoric acid in 1.0 liter of 2-methylpropanol, followed by supply of 2.4 liters of 2-methylpropanol. The 89% phosphoric acid was substantially composed of orthophosphoric acid alone. This slurry was further heated under reflux for 7 hours and then cooled. The resultant product was washed with 2-methylpropanol, filtered and dried at 130° C. for 10 hours to produce a catalyst precursor.

Example 10

A catalyst precursor was produced in the same way as Example 9 except that the initial reflux (pre-reflux) was conducted for one hour.

Example 11

5,120 g of 2-methylpropanol, 205.4 g of benzyl alcohol, 347.5 g of vanadium pentoxide and 36.0 g of ferrous oxalate dihydrate were placed in a 10-liter vessel and heated under reflux in a slurry state for 3 hours. To this slurry was added a solution of 528.5 g of commercial 89% phosphoric acid in 1.0 liter of 2-methylpropanol, and then 0.1 liter of 2-methylpropanol was supplied. The commercial 89% phosphoric acid was substantially composed of orthophosphoric acid alone. This slurry was further heated under reflux for 7 hours and cooled. The resultant product was washed with 2-methylpropanol, filtered and dried at 130° C. for 10 hours to produce a catalyst precursor.

Example 12

2,195 g of 2-methylpropanol, 347.5 g of vanadium pentoxide and 36.0 g of ferrous oxalate dihydrate were placed in a 10-liter vessel and heated under reflux in a slurry state for 3 hours. To this slurry was added a solution of 205.4 g of benzyl alcohol and 528.5 g of commercial 89% phosphoric acid in 1.0 liter 2-methylpropanol. The commercial 89% phosphoric acid was substantially composed of orthophosphoric acid alone. After supplying 2.4 liters of 2-methylpropanol, the slurry was heated under reflux for 7 hours and then cooled. The resultant product was washed with 2-methylpropanol, filtered and dried at 130° C. for 10 hours to produce a catalyst precursor.

Example 13

2,400 g of 2-methylpropanol and 347.5 g of vanadium pentoxide were placed in a 10-liter vessel and heated under reflux in a slurry state for 3 hours. To this slurry was added a solution of 528.5 g of commercial 89% phosphoric acid in 1.0 liter of 2-methylpropanol, and then 2.4 liters of 2-methylpropanol was supplied. The commercial 89% phosphoric acid was substantially composed of orthophosphoric acid alone. Concurrently with start of reflux of the slurry, 36.0 g of ferrous oxalate dihydrate was added and the slurry was heated under reflux for 7 hours and then cooled. The resultant product was washed with 2-methylpropanol, filtered and dried at 130° C. for 10 hours to produce a catalyst precursor.

Example 14

2,400 g of benzyl alcohol, 347.5 g of vanadium pentoxide and 36.0 g of ferrous oxalate dihydrate were placed in a 10-liter vessel and heated under reflux in a slurry state for 3 hours. To this slurry was added a mixed solution of 528.5 g of commercial 89% phosphoric acid and 1,000 g of benzyl alcohol, followed by supply of 1,720 g of benzyl alcohol. The commercial 89% phosphoric acid was substantially composed of orthophosphoric acid alone. This slurry was heated at 80° C. for 7 hours and cooled. The resultant product was washed with 2-methylpropanol, filtered and dried at 130° C. for 10 hours to produce a catalyst precursor.

Example 15

A catalyst precursor was produced in the same way as Example 9 except that the amounts of 2-methylpropanol, benzyl alcohol, vanadium pentoxide and ferrous oxalate dihydrate were changed to 2,205 g, 194.6 g, 329.2 g and 72.0 g, respectively.

Example 16

A catalyst precursor was produced in the same way as Example 15 except that the amounts of first used 2-methylpropanol and benzyl alcohol were changed to 2,011 g and 389.3 g, respectively.

Example 7

A catalyst precursor was produced in the same way as Example 9 except that the amounts of first used 2-methylpropanol, benzyl alcohol, vanadium pentoxide and ferrous oxalate dihydrate were changed to 2,205 g, 194.6 g, 292.6 g and 144.0 g, respectively.

Example 18

A catalyst precursor was produced in the same way as Example 9 except for use of 38.2 g of ferrous acetate in place of ferrous oxalate.

Example 19

The procedure of Example 9 was followed except for use of 40.2 g of ferric phosphate in place of ferrous oxalate to produce a catalyst precursor.

Comparative Example 12

2,400 g of 2-methylpropanol, 329.2 g of vanadium pentoxide and 72.0 g of ferrous oxalate dihydrate were placed in a 10-liter vessel and heated under reflux for 3 hours. To the resultant slurry was added a solution of 553.4 g of 85% phosphoric acid in 1.0 liter of 2-methylpropanol, followed by supply of 2.4 liters of 2-methylpropanol. The slurry was heated under reflux for 7 hours and then cooled. The resultant product was washed with 2-methylpropanol, filtered and dried at 130° C. for 10 hours to produce a catalyst precursor.

Comparative Example 13

2,400 g of 2-methylpropanol, 329.2 g of vanadium pentoxide and 72.0 g of ferrous oxalate dihydrate were placed in a 10-liter vessel and heated under reflux in a slurry state for 3 hours. To this slurry was added a solution of 475.2 g of solid phosphoric acid (purity: 99%) in 1.0 liter of 2-methylpropanol, followed by supply of 2.4 liters of 2-methylpropanol. This slurry was heated under reflux for 7 hours and then cooled. The resultant product was washed With 2-methylpropanol, filtered and dried at 130° C. for 10 hours to produce a catalyst precursor.

Reaction Test 3

The oxide catalyst precursors obtained in Examples 9–18 and Comparative Examples 1, 12 and 13 were subjected to the same activity test as conducted in Reaction Test 1. The results are shown in Table 3. The catalysts of the Examples according to the present invention provide a higher yield of maleic anhydride, act even at a lower reaction temperature and give better reaction results compared with the catalysts of the Comparative Examples.

Example 20

2,195 g of 2-methylpropanol, 205.4 g of benzyl alcohol, 347.5 g of vanadium pentoxide and 36.0 g of ferrous oxalate dihydrate were placed in a 10-liter vessel and heated under reflux in a slurry state for 3 hours. To this slurry was added a solution of 528.5 g of commercial 89% phosphoric acid in 1.0 liter of 2-methylpropanol, followed by supply of 2.4 liters of 2-methylpropanol. The commercial 89% phosphoric acid was substantially composed of orthophosphoric acid alone. The slurry was further heated under reflux for 7 hours, during which time an aqueous layer portion alone was removed, by a total amount of 67 ml, from a distillate through a Dean-Stark trap. The reaction slurry was cooled, filtered and dried at 130° C. for 10 hours to produce a catalyst precursor.

Example 21

A catalyst precursor was produced in the same way as Example 20 except that total 60 ml of the aqueous layer was removed during the 7-hour heating under reflux.

Comparative Example 14

A catalyst precursor was produced in the same way as Example 20 except for use of 475.2 g of solid phosphoric acid (purity: 99%). During the 7-hour heating under reflux, total 14.5 ml of the aqueous layer was removed.

Reaction Test 4

The oxide catalyst precursors obtained in Examples 20 and 21 and Comparative Examples 9, 10 and 14 were calcined under a nitrogen atmosphere at 550° C. and molded into particles of 14–24 mesh in size, and these catalyst particles were subjected to the same activity test as conducted in Reaction Test 1. The results are shown in Table 4.

TABLE 3

| | Production conditions | | | | Reaction results | | |
|---|---|---|---|---|---|---|---|
| | Phosphoric acid concentration (%) | Ratio of added iron 1) | Ratio of added benzyl alcohol 2) | Pre-reflux time (hr) | Reaction temperature 3) (°C.) | n-Butane conversion 4) (%) | Yield of maleic anhydride 5) (%) |
| Example 9 | 89 | 0.05 | 1.0 | 3 | 377 | 91.5 | 51.4 |
| Example 10 | 89 | 0.05 | 1.0 | 1 | 387 | 90.5 | 53.7 |
| Example 11 | 89 | 0.05 | 1.0 | 3 | 377 | 90.9 | 53.1 |
| Example 12 | 89 | 0.05 | 1.0 | 3 | 362 | 91.8 | 52.2 |
| Example 13 | 89 | 0.05 | 0 | 3 | 373 | 90.4 | 50.2 |
| Example 14 | 89 | 0.05 | 24.9 | 3 | 380 | 91.7 | 54.9 |
| Example 15 | 89 | 0.10 | 1.0 | 3 | 379 | 90.4 | 52.3 |
| Example 16 | 89 | 0.10 | 2.0 | 3 | 387 | 89.0 | 50.9 |
| Example 17 | 89 | 0.20 | 1.1 | 3 | 376 | 88.1 | 48.7 |
| Example 18 | 89 | 0.05 | 0 | 3 | 383 | 91.6 | 53.1 |
| Example 19 | 89 | 0.05 | 0 | 3 | 390 | 90.0 | 51.2 |
| Comp. Example 1 | 85 | 0.05 | 0 | 3 | 386 | 90.0 | 47.0 |
| Comp. Example 12 | 85 | 0.16 | 0 | 3 | 423 | 86.0 | 33.4 |
| Comp. Example 13 | Solid | 0.05 | 0 | 3 | 425 | 83.5 | 37.0 |

1) Fe/(Fe + V) atomic ratio
2) Benzyl alcohol/vanadium pentoxide molar ratio
3) Reaction temperature at 85% conversion of n-butane
4) Conversion at the time of maxima yield of maleic anhydride
5) Maximum yield of maleic anhydride

TABLE 4

| | Production conditions | | | Reaction results | | |
|---|---|---|---|---|---|---|
| | Phosphoric acid concentration (%) | Ratio of added iron 1) | Amount of water removed (ml) | Reaction temperature 2) (°C.) | n-Butane conversion 3) (%) | Yield of maleic anhydride 4) (%) |
| Example 20 | 89 | 0.05 | 67 | 373 | 92.4 | 54.7 |
| Example 21 | 89 | 0.05 | 60 | 367 | 91.0 | 52.1 |
| Comp. example 9 | 85 | 0.05 | 71 | 374 | 89.8 | 48.2 |
| Comp. example 10 | Solid | 0 | 65 | 418 | 85.5 | 39.7 |
| Comp. example 14 | Solid | 0.05 | 15 | 412 | 93.5 | 43.3 |

1) Fe/(Fe + V) atomic ratio
2) Reaction temperature at 85% conversion of n-butane
3) Conversion at the time of maximum yield of maleic anhydride
4) Maximum yield of maleic anhydride Example 22

<Preparation of vanadyl phosphate solution>
10.54 kg of 85% phosphoric acid and 10.743 kg of oxalic acid dihydrate were added to 10 kg of desalted water and dissolved by stirring under heating to 80° C. Then 7.75 kg of vanadium pentoxide was added little by little while giving attention to foaming. The reaction was carried out at 95° to 100° C. for 0.5 hours. After cooling, water was added to the mixture to make its total amount 38.5 kg. This solution had a P/V atomic ratio of 1.08 and contained 0.5 gram mol. of oxalic acid per gram atom of vanadium.
<Production of catalyst>
First step:
A catalyst precursor was produced in the same way as Example 9 The process was repeated 5 times to obtain about 3.5 kg of the product.
Second step:
The product was dry-pulverized by a single track jet mill manufactured by Seishin Kigyo KK, using 3 KG (kg/cm$^2$-G) pressurized air.
Third step:
3.39 kg of the particles obtained by Jet milling in the above second step were mixed with 3,288 g of the said vanadyl phosphate solution and 7.32 kg of water to form a slurry (Component A (particles obtained in the second step): 70%; Component B (vanadyl phosphate - amorphous vanadium/phosphorus oxides): 30%, as expressed in an amount after dried and calcined). This slurry was introduced into a disc rotary type spray dryer to form particles. 4.0 kg of the obtained particles were calcined by a fluid furnace, under a nitrogen gas flow, at 550° C. for 2 hours to produce a catalyst.

Comparative Example 15

A catalyst precursor was produced in the same way as Example 22 except for use of the catalyst precursor obtained in Comparative Example 1.

Example 23

A catalyst precursor was produced in the same way as Example 22 except for use of the catalyst precursor obtained in Example 2.

Example 24

2,195 g of 2-methylpropanol, 205.4 g of benzyl alcohol, 347.5 g of vanadium pentoxide and 36.0 g of ferrous oxalate dihydrate were placed in a 10-liter vessel and heated under reflux in a slurry state for 3 hours. To this slurry was added a solution of 528.5 g of 89% phosphoric acid in 1.0 liter of 2-methylpropanol, followed by supply of 2.4 liters of 2-methylpropanol. The 89% phosphoric acid was substantially composed of orthophosphoric acid alone. This slurry was further heated under reflux for 7 hours during which time an aqueous layer portion alone was removed, by a total amount of about 65 ml, from a distillate through a Dean-Stark trap. The slurry was cooled and filtered, and the resultant product was washed with 2-methylpropanol, filtered and dried at 130° C. for 10 hours. The above process was repeated 5 times to obtain about 3.5 kg of product. By using this product, a catalyst was produced in the same way as Example 22 except for the first step.

Example 25

21.95 kg of 2-methylpropanol, 2,054 g of benzyl alcohol, 3,475 g of vanadium pentoxide and 360 g of ferrous oxalate dihydrate were placed in a 120-liter glass-lined vessel and heated under reflux in a slurry state for 3 hours. To this slurry was added a solution of 5,285 g of 89% phosphoric acid in 10 liters of 2-methylpropanol, and then 24 liters of 2-methylpropanol was supplied. The 89% phosphoric acid was substantially composed of orthophosphoric acid alone. This slurry was further heated under reflux for 7 hours and then cooled. The resultant product was washed with 2-methylpropanol, filtered and dried at 80° C. for 15 hours. By using this product, a catalyst was produced in the same way as Example 22 except for the first step.

Reaction Test 5

The catalyst particles obtained in Examples 22–25 and Comparative Example 15 were subjected to the following catalytic activity test. 650 g of the catalyst particles within a predetermined range of particle size were placed in a fluid bed reactor having a tray with an inner diameter of 42 mm and a length of about 1.5 m and reaction was conducted under the conditions of 4.0% butane concentration, 1.5 kg/cm$^2$-G and 720 GHSV. A life test was continued by adjusting a reaction temperature so that the butane conversion would become 85% or above. For determining the reaction results, a reaction outlet gas was absorbed in water and the amount of maleic anhydride produced was measured by titration. Also, the reaction gas which has not been absorbed in water was sampled and analyzed by gas chromatography. The results obtained after about 800 hours from the start of the reaction are shown in Table 5. When the catalysts of the Examples were used, the yield of maleic anhydride is higher and the reaction temperature is the same as or higher, so better reaction results are obtained, compared with the catalyst of the Comparative Example.

TABLE 5

| Catalyst Phosphorus source in preparation of precursor | Reaction results | |
|---|---|---|
| | Reaction temp. 1) | Yield of maleic anhydride 2) |
| Example | | |
| 22  89% Phosphoric acid | 436° C. | 51.8% |
| 23  95% Phosphoric acid | 440° C. | 52.9% |
| 24  89% Phosphoric acid Water removed | 435° C. | 52.4% |
| 25  89% Phosphoric acid | 437° C. | 52.2% |
| Comp. example 15  85% Phosphoric acid | 440° C. | 49.8% |

1) Reaction temperature at 85% conversion of n-butane
2) Maximum yield of maleic anhydride

What is claimed is:

1. A process for producing a precursor of a phosphorus-vanadium oxide catalyst for production of maleic anhydride by vapor phase oxidation of a hydrocarbon having 4 carbon atoms, which comprises reacting phosphoric acid and a pentavalent vanadium compound in an organic solvent capable of reducing at least a portion of the pentavalent vanadium to a valence state of +4, the phosphoric acid being substantially composed of orthophosphoric acid, and a phoshoric acid solution whose concentration is 88 to 96% being used as a source of the phosphoric acid.

2. A process according to claim 1, wherein the concentration of the aqueous phosphoric acid solution is more than 90% and not more than 96%.

3. A process according to claim 1, wherein the aqueous phosphoric acid solution is prepared by adding water to an aqueous 105% phosphoric acid solution.

4. A process according to claim 1, wherein a concentration of the aqueous phosphoric acid solution is 88 to 90%.

5. A process according to claim 1, wherein the pentavalent vanadium compound is selected from the group consisting of vanadium pentoxide, ammonium metavanadate and vanadium oxytrihalide.

6. A process according to claim 1, wherein the pentavalent vanadium compound is vanadium pentoxide.

7. A process according to claim 1, wherein the organic solvent is a mixture of an aliphatic alcohol having 3 to 6 carbon atoms and benzyl alcohol.

8. A process according to claim 1, wherein a ratio of phosphoric acid to the pentavalent vanadium compound, determined as a phosphorus to vanadium atomic ratio (P:V), is P:V=1.0:1 to 1.3:1.

9. A process according to claim 1, which comprises adding iron, cobalt or zinc as a cocatalyst.

10. A process according to claim 9, wherein an amount of the cocatalyst, determined as an atomic ratio to a sum of the vanadium and the cocatalyst metal, is 0.005:1 to 0.3:1.

11. A process according to claim 7, wherein an amount of benzyl alcohol, determined as a molar ratio to the pentavalent vanadium compound, is 0.02:1 to 2:1.

12. A process according to claim 1, wherein water is removed during the reaction.

13. A process according to claim 1, wherein the reaction is carried out by slurring the pentavalent vanadium compound in the reducing organic solvent, heating the obtained slurry at 80° to 200° C. then adding the phosphoric acid, and further heating the resultant slurry for 1 to 20 hours.

14. A process for producing a phosphorus-vanadium oxide catalyst for production of maleic anhydride by vapor phase oxidation of a hydrocarbon having 4 carbon atoms, which comprises the steps of (1) reacting phosphoric acid and a pentavalent vanadium compound in an organic solvent capable of reducing at least a portion of the pentavalent vanadium to a valence state of +4, the phosphoric acid being substantially composed of orthophosphoric acid, and a phoshoric acid solution whose concentration is 88 to 96% being used as a source of the phosphoric acid, to produce a catalyst precursor; (2) dry-pulverizing the obtained catalyst precursor in a high-speed gas flow; and (3) mixing the pulverized material with an aqueous solution containing phosphorus and tetravalent vanadium to form a slurry, and drying the obtained slurry and calcining.

15. A process according to claim 14, wherein the pentavalent vanadium compound is selected from the group consisting of vanadium pentoxide, ammonium metavanadate and vanadium oxytrihalide.

16. A process according to claim 14, wherein the pentavalent vanadium compound is vanadium pentoxide.

17. A process according to claim 14, wherein the organic solvent is a mixture of an aliphatic alcohol having 3 to 6 carbon atoms and benzyl alcohol.

18. A process according to claim 14, wherein a ratio of phosphoric acid to the pentavalent vanadium compound, determined as a phosphorus to vanadium atomic ratio (P:V), is P:V=1.0:1 to 1.3:1.

19. A process according to claim 14, which comprises adding iron, cobalt or zinc as a cocatalyst.

20. A process according to claim 19, wherein an amount of the cocatalyst, determined as an atomic ratio to a sum of the vanadium and the cocatalyst metal, is 0.005:1 to 0.3:1.

21. A process according to claim 17, wherein an amount of benzyl alcohol, determined as a molar ratio to the pentavalent vanadium compound, is 0.02:1 to 2:1.

22. A process according to claim 14, wherein water is removed during the reaction.

23. A process according to claim 14, wherein dry-pulverizing in a high-speed gas flow is carried out by a gas whose applied pressure is 3 to 10 KG.

24. A process according to claim 14, wherein a particle size of the pulverized material after the dry-pulverizing in a high-speed gas flow is 0.5 to 2.0 μm (weight-average diameter).

25. A process according to claim 14, wherein the aqueous solution containing phosphorus and tetravalent vanadium is a vanadyl phosphate solution.

26. A process according to claim 14, wherein the calcination is carried out at 350° to 700° C. for 0.1 to 20 hours.

27. A process for producing maleic anhydride by vapor phase oxidation of a hydrocarbon having 4 carbon atoms in the presence of a catalyst produced by using a phosphorus-vanadium oxide catalyst precursor obtainable by reacting phosphoric acid and a pentavalent vanadium compound in an organic solvent capable of reducing at least a portion of the pentavalent vanadium to a valence state of +4, the phosphoric acid being substantially composed of orthophosphoric acid, and a phoshoric acid solution whose concentration is 88 to 96% being used as a source of the phosphoric acid.

* * * * *

UNITED STATES PATENT AND TRADEMARK OFFICE
CERTIFICATE OF CORRECTION

PATENT NO. : 5,530,144
DATED : JUNE 25, 1996
INVENTOR(S) : YASUSHI TSURITA ET AL

It is certified that error appears in the above-indentified patent and that said Letters Patent is hereby corrected as shown below:

Column, 2, lines 3-4, "62-61951 (1987)" should read --2-61951 (1990)--; and
line 4, "4,3.65,069 and 4,448,873" should read --4,365,069 and 4,448,893--.

Signed and Sealed this

Fifteenth Day of October, 1996

Attest:

BRUCE LEHMAN

*Attesting Officer*   *Commissioner of Patents and Trademarks*